(12) United States Patent
Hayashi

(10) Patent No.: US 6,280,464 B1
(45) Date of Patent: *Aug. 28, 2001

(54) PROSTHESIS GRIPPING SYSTEM AND METHOD

(75) Inventor: Reid Hayashi, Palo Alto, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/326,988

(22) Filed: Jun. 7, 1999

Related U.S. Application Data

(63) Continuation of application No. 09/005,122, filed on Jan. 9, 1998, now Pat. No. 5,910,144.

(51) Int. Cl.⁷ .............................. A61F 11/00; A61F 2/06
(52) U.S. Cl. ........................................ 623/1.11; 606/108
(58) Field of Search .................................. 606/108, 191, 606/192, 194, 198, 206; 623/1, 11, 12, 1.11, 1.12; 604/95, 53; 600/205, 129, 130, 203, 218, 224

(56) References Cited

U.S. PATENT DOCUMENTS

| | | | |
|---|---|---|---|
| 2,549,731 | * | 4/1951 | Wattley ................................. 439/482 |
| 3,950,022 | | 4/1976 | Florh . |
| 4,174,548 | | 11/1979 | Dunn . |
| 4,655,219 | * | 4/1987 | Petruzzi ............................... 606/206 |
| 4,830,002 | | 5/1989 | Semm . |
| 4,909,789 | * | 3/1990 | Taguchi et al. ....................... 606/107 |
| 5,201,757 | | 4/1993 | Heyn et al. . |
| 5,203,772 | | 4/1993 | Hammerslag et al. . |
| 5,352,237 | | 10/1994 | Rodak et al. . |
| 5,649,906 | | 7/1997 | Gory et al. . |
| 5,713,948 | | 2/1998 | Uflacker . |
| 5,910,144 | * | 6/1999 | Hayashi ............................... 606/108 |

* cited by examiner

Primary Examiner—Henry J. Recla
Assistant Examiner—Vy Q. Bui
(74) Attorney, Agent, or Firm—Fulwider Patton Lee & Utecht, LLP

(57) ABSTRACT

A delivery catheter and gripping system for enabling manipulation of a prosthesis deployed or implanted at a repair site in a corporeal lumen, for repositioning of the prosthesis. The delivery catheter includes a grip at the proximal end, a jacket enlarged portion at the distal end, and a shaft therebetween, and has a channel extending therethrough, for enabling insertion, removal, expansion and compression of the gripping system. The gripping system is housed in the delivery catheter, and includes a grip and biasing spring at the proximal end, a plurality of resilient gripping elements at the distal end, and a deploying wire therebetween for enabling gripping, maneuvering, and repositioning of the prosthesis to the desired location. The catheter jacket is retracted from enclosing the gripping elements, enabling the gripping elements to expand about the prosthesis end, and is then advanced to compress the gripping elements into engagement with the prosthesis end for maneuvering thereof so as to reposition the prosthesis.

18 Claims, 5 Drawing Sheets

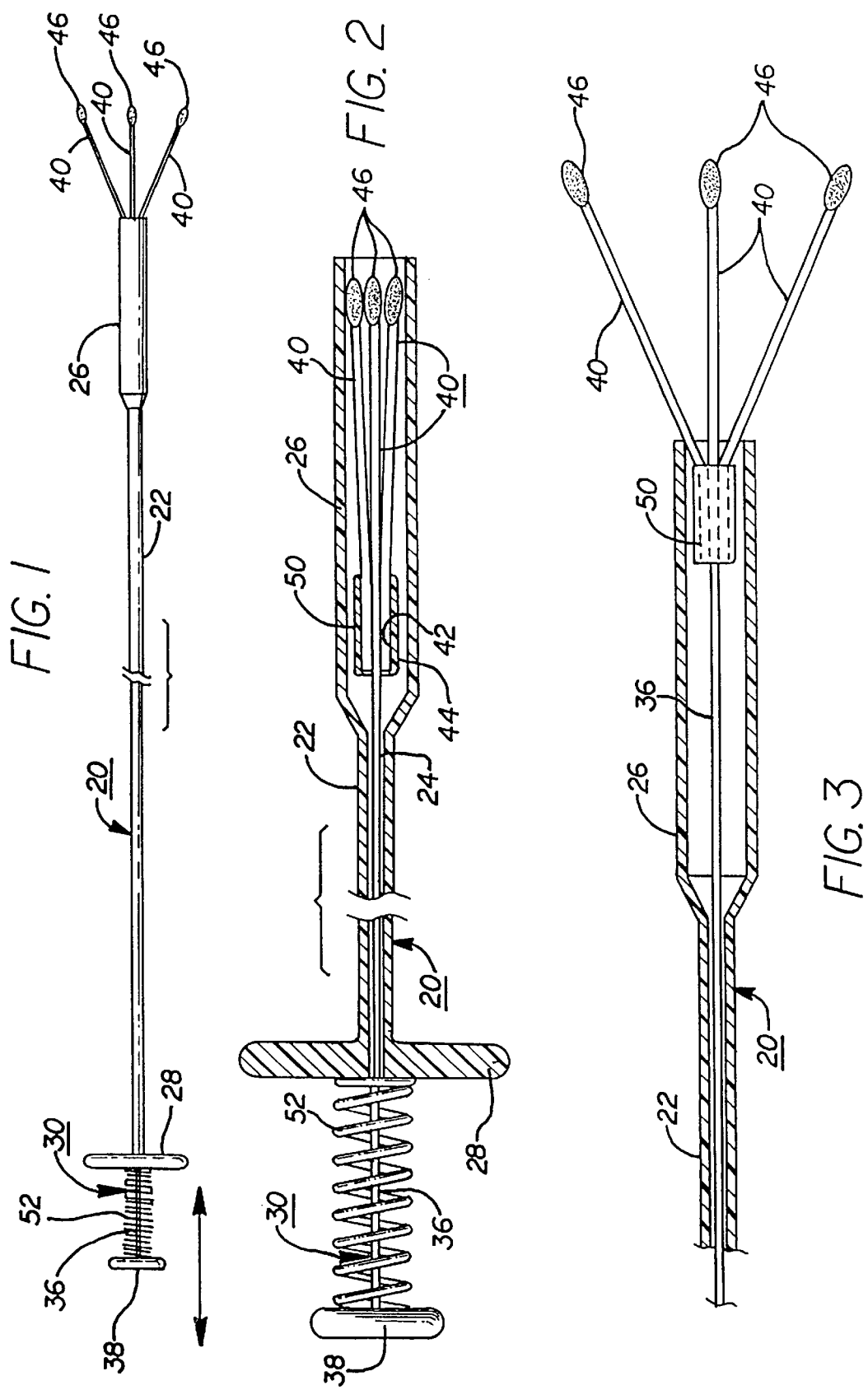

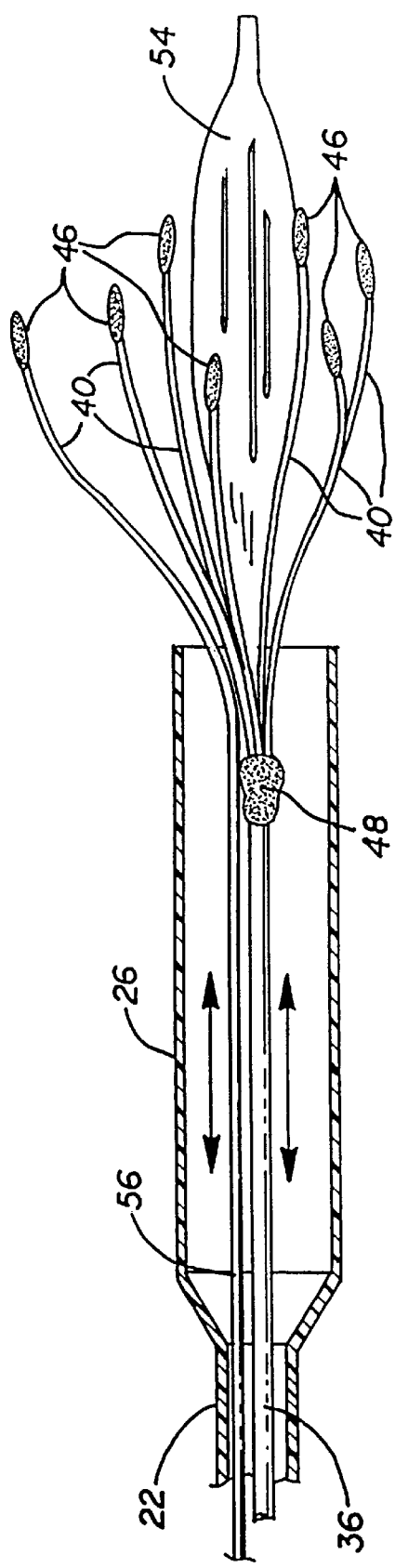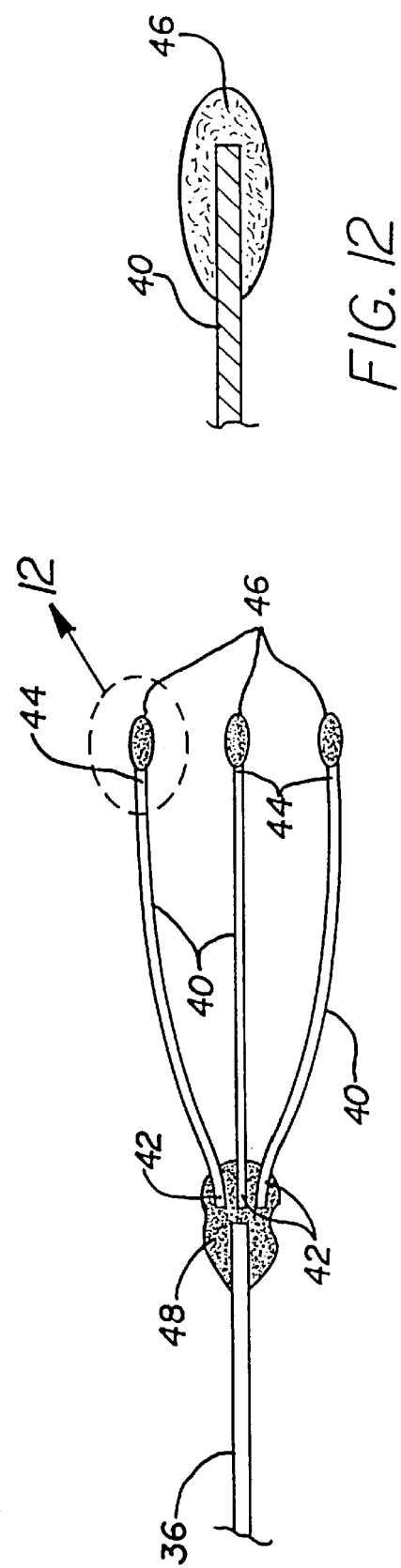
FIG. 10
FIG. 11
FIG. 12

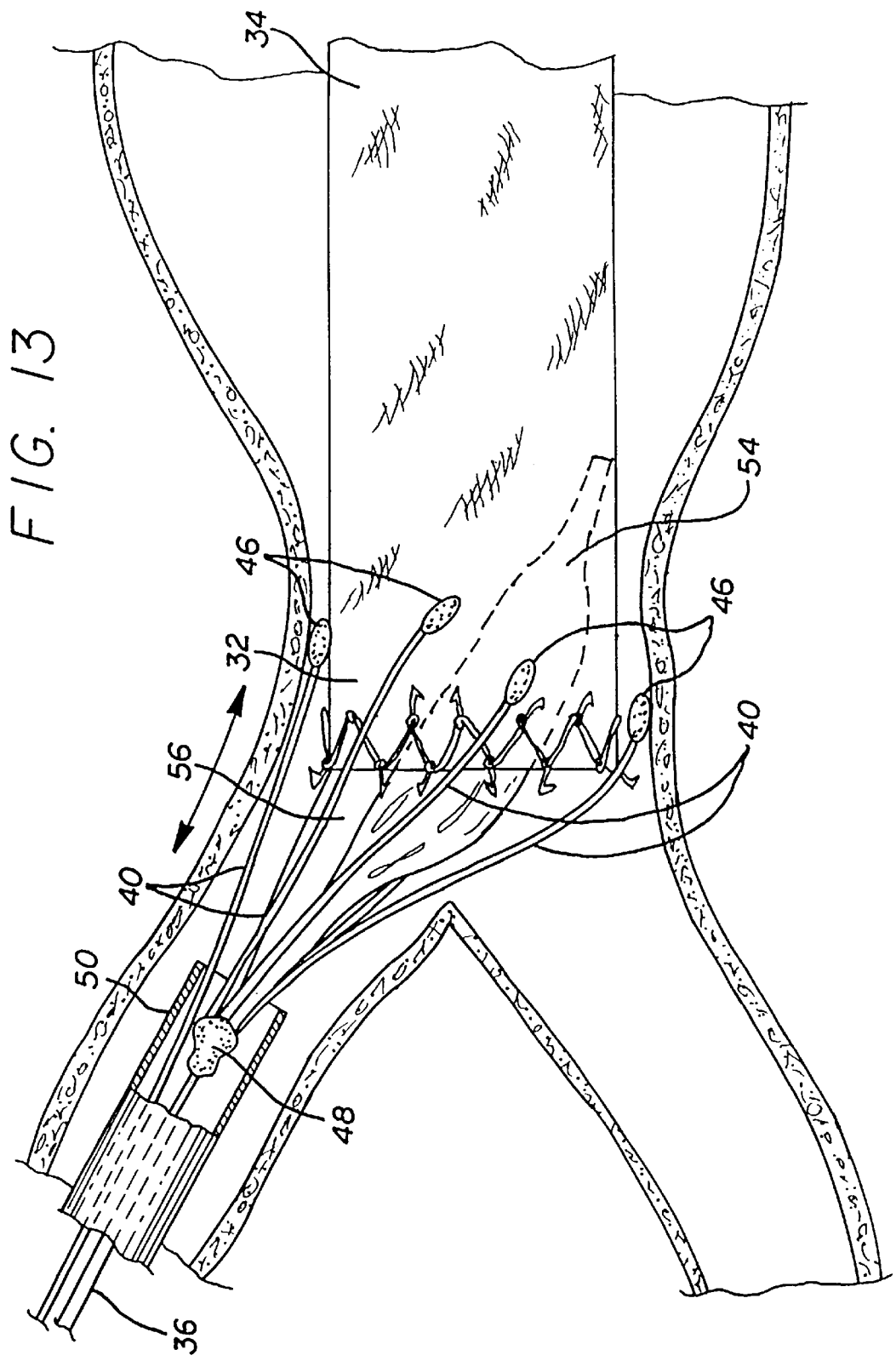

PROSTHESIS GRIPPING SYSTEM AND METHOD

This is a continuation of application Ser. No. 09/005,122, filed Jan. 9, 1998, now U.S. Pat. No. 5,910,144.

BACKGROUND OF THE INVENTION

This invention relates to a system for manipulating a prosthesis, and more particularly, to a catheter and gripping system for enabling manipulation of a graft or stent deployed or implanted at a repair site within a corporeal lumen.

It is well established that various fluid conducting body or corporeal lumens, such as veins and arteries, may deteriorate or suffer trauma so that repair is necessary. For example, various types of aneurysms or other deteriorative diseases may affect the ability of the lumen to conduct fluids and, in turn, may be life-threatening. In some cases, the damaged lumen is repairable only with the use of a prosthesis such as an artificial vessel or graft. Other situations require the use of a stent which operates to hold a constricted vessel open. For repair of vital vessels such as the aorta, repair may be significantly life-threatening.

Techniques known in the art which tend to minimize dangers to the patient include a procedure in which a graft resembling the natural vessel is placed within the diseased or obstructed section of the natural vessel. More specifically, it is known within the art to provide a graft for intraluminal repair of a vessel. In intraluminal vessel repair, the graft is advanced intraluminally through the vessel to the repair site using a delivery catheter and deployed within the vessel so that the graft traverses the diseased portion to thereby repair the vessel.

Additionally, it is known within the art to provide a stent for holding open a vessel which is constricted due to a stenosis. In order to minimize danger to the patient, a stent may also be intraluminally deployed.

Generally speaking, it may be necessary to reposition a graft or stent deployed or implanted at a repair site in a corporeal lumen. However, it may be difficult to maneuver a device to a position adjacent the prosthesis, to grip the prosthesis for maneuvering thereof to the desired location, and to then retrieve the device from the repair site.

Thus, what has been needed and heretofore unavailable is a system which is designed specifically to enable secure gripping and maneuvering of a prosthesis which has been placed within a patient's vasculature and to accomplish repositioning of the prosthesis within the patient's vasculature to a desired location.

SUMMARY OF THE INVENTION

Briefly, and in general terms, the present invention provides a new and improved catheter and gripping system, and a novel method for their use in manipulating a prosthesis or repair device at a repair site in a corporeal lumen. The prosthesis or repair device is deployed or implanted at the lumen repair site for repairing a diseased condition of the lumen. The catheter and gripping system is configured to enable secure gripping and manipulation of the prosthesis at the repair site, for repositioning the prosthesis to the desired location.

The present catheter is adapted to enable insertion and removal thereof in a corporeal lumen. It includes a grip at a proximal end for enabling gripping thereof, a jacket at a distal end thereof comprising an enlarged portion for enclosing and enabling expansion and compression of gripping elements, and a shaft therebetween, including a channel extending therethrough.

The present gripping system is housed in the catheter and is adapted to enable gripping of the prosthesis end at the repair site in the corporeal lumen, for maneuvering and repositioning the prosthesis to the desired location. It includes a knob at a proximal end for enabling pushing thereof for compressing the gripping elements into engagement with the prosthesis end. A spring extends between the knob and the catheter grip for biasing the system so as to normally enclose the gripping elements. A plurality of resilient gripping elements at the distal end of the system are adapted to engage the prosthesis end. The gripping elements are biased to an open or spread-out configuration and include angled ends for gripping a prosthesis end. A deploying wire extends between the knob and the gripping elements.

A method contemplated for repositioning the prosthesis at the repair site in the corporeal lumen includes retracting the catheter jacket from its position enclosing the gripping elements, releasing the gripping elements for outward expansion thereof. The catheter jacket is then advanced, compressing the gripping elements so as to engage the graft end. The jacket is then retracted, enabling the gripping elements to expand, and then advanced to compress and enclose the gripping elements to enable removal of the system from the corporeal lumen. Another method further includes advancing a folded balloon at the distal end of the gripping system into engagement with the prosthesis end, for enabling secure gripping of the prosthesis end by the gripping elements. A further method also includes actuating a maneuverable element into engagement with the prosthesis end.

Other features and advantages of the present invention will become apparent from the following detailed description, taken in conjunction with the accompanied drawings, which illustrate, by way of example, the features of the invention.

BRIEF DESCRIPTION OF THE DRAWINGS

FIG. 1 is an elevational view of a catheter and prosthesis gripping system incorporating a first embodiment of the present invention.

FIG. 2 is an elevational partly-sectional view of the catheter and prosthesis gripping system incorporating the first embodiment of the present invention, with the gripping elements enclosed.

FIG. 3 is an elevational partly-sectional view of the catheter and prosthesis gripping system incorporating the first embodiment of the present invention, with the gripping elements expanded.

FIG. 10 is an elevational partly-sectional partly-fragmentary view of a catheter and prosthesis gripping system incorporating a third embodiment of the present invention, with a maneuverable gripping element in expanded condition.

FIG. 11 is an elevational partly-fragmentary view of a bead connecting a deploying wire and gripping elements in the present invention.

FIG. 12 is a gragmentary view of the distal end and tip of a gripping element in the present invention.

FIG. 13 is an elevational partly-fragmentary partly-sectional view of the third embodiment of the present invention, with the maneuverable gripping element compressed into gripping engagement with the prosthesis end.

DETAILED DESCRIPTION OF THE PREFERRED EMBODIMENTS

Figure 4:
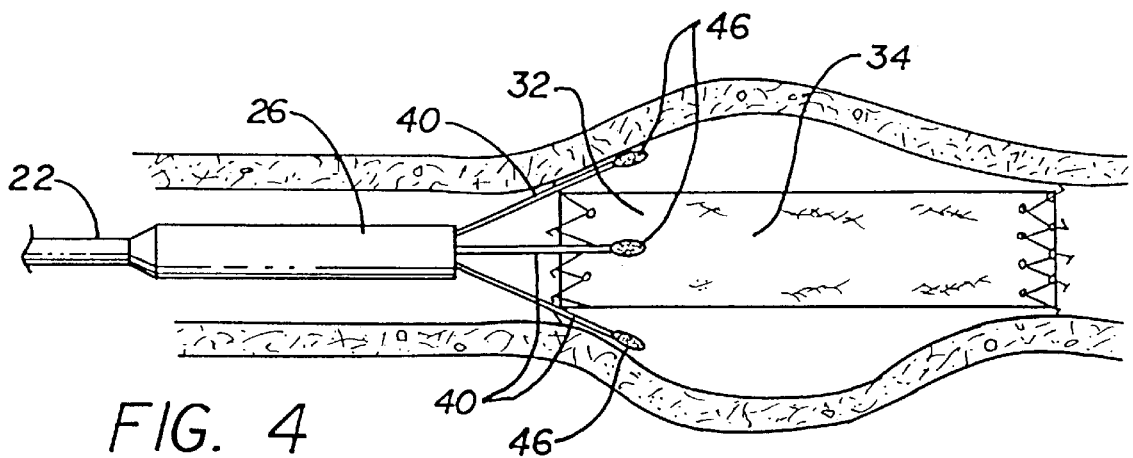
FIG. 4 is an elevational partly-sectional view of the catheter and prosthesis gripping system incorporating the first embodiment of the present invention, with the gripping elements expanded about an end of a prosthesis in a corporeal lumen.

As shown in the drawings and for purposes of illustration, the invention is embodied in a gripping system for enabling manipulation of a prosthesis deployed or implanted in a corporeal lumen at a repair site, and a catheter for the prosthesis gripping system. One of the novel features of the present invention is the gripping system which operates to securely grip the prosthesis within the corporeal lumen at the repair site to enable manipulation of the prosthesis, for repositioning the end of the prosthesis to the desired location. Another novel feature of the present invention is the actuating and releasing system which functions to actuate the gripping and release of the prosthesis for manipulation and release of the prosthesis.

Generally, in the present invention, the prosthesis manipulating system is comprised of a prosthesis gripping system including gripping elements which are actuatable and releasable. The gripping elements are biased open end including angled ends for facilitating grabbing a prosthesis. The gripping elements further include distal tips which engage with and release from the end of the prosthesis. A biased push knob and grip are provided for enabling actuation and release of the gripping elements. The delivery catheter includes an enlarged distal end portion, for enabling retraction of the gripping elements therein for insertion and removal thereof in the corporeal lumen.

Figure 5:
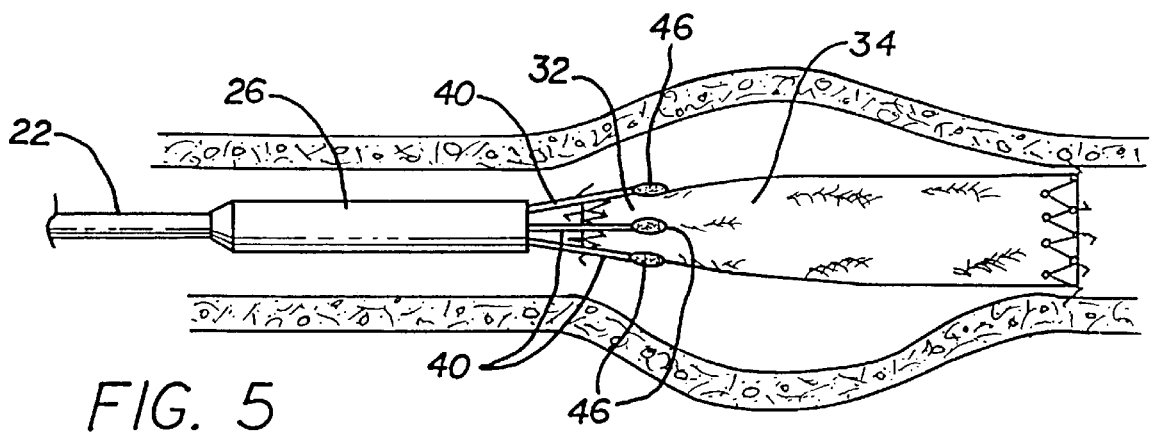
FIG. 5 is an elevational partly-sectional view of the catheter and prosthesis gripping system incorporating the first embodiment of the present invention, with the gripping elements compressed into engagement with the end of the graft in the corporeal lumen.
Figure 6:
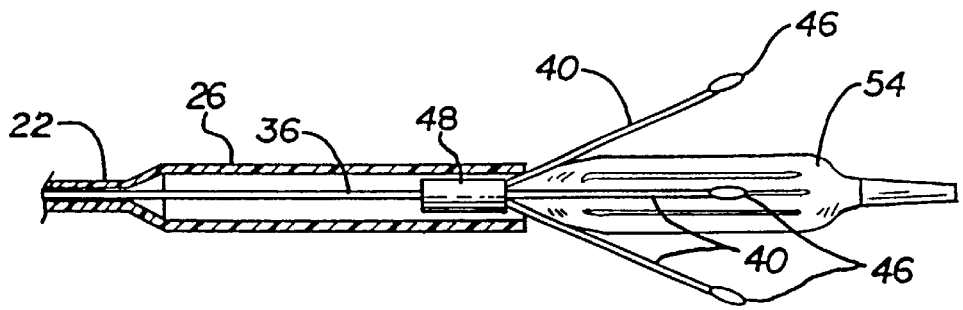
FIG. 6 is an elevational partly-sectional view of the catheter and prosthesis gripping system incorporating the second embodiment of the present invention, with the gripping elements expanded.
Figure 7:
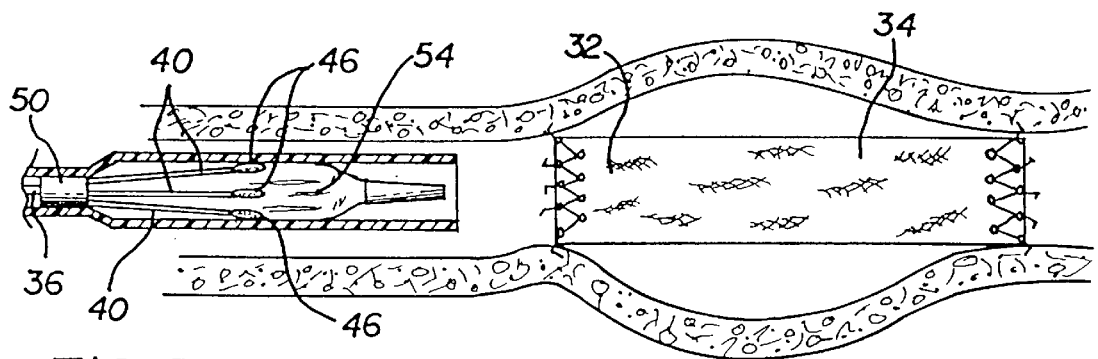
FIG. 7 is an elevational partly-sectional view of the catheter and prosthesis gripping system incorporating the second embodiment of the present invention, with the gripping elements enclosed proximate an end of a prosthesis in a corporeal lumen.
Figure 8:
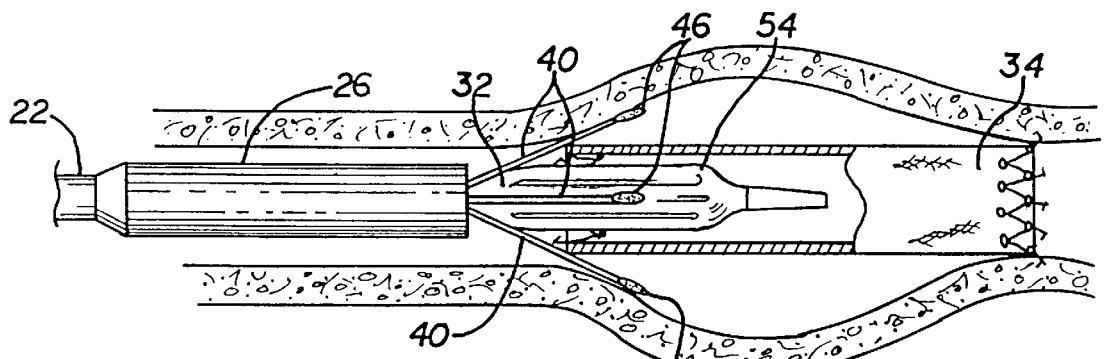
FIG. 8 is an elevational partly-sectional view of the catheter and prosthesis gripping system incorporating the second embodiment of the present invention, with the gripping elements expanded about an end of the prosthesis in the corporeal lumen, and the balloon in position engaging the prosthesis end.
Figure 9:
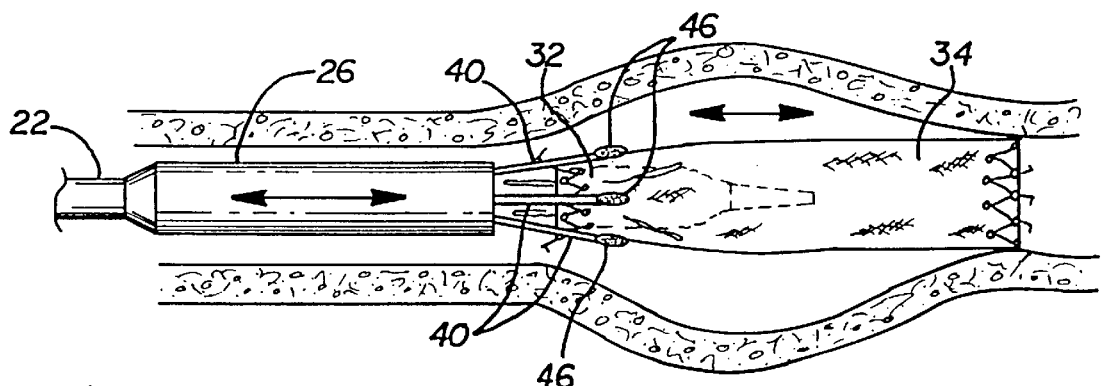
FIG. 9 is an elevational partly-sectional view of the catheter and prosthesis gripping system incorporating the second embodiment of the present invention, with the gripping elements compressed into the end of the prosthesis in the corporeal lumen, and the balloon in prosthesis engaging position.

In more detail, the catheter 20 is shown in FIGS. 1–10 and 13. In particular, as shown in FIG. 2, the catheter 20 includes an elongated tubular shaft 22 which includes a channel 24 extending therethrough, a jacket 26 at the distal end of catheter 20, and a generally disk-shaped grip 28 at the proximal end thereof.

FIGS. 1–5 show a first preferred embodiment of catheter 20 and a system 30 reciprocally movable in catheter 20 for manipulating an end 32 of a prosthesis 34. End 32 of prosthesis 34 is preferably comprised of compressible material and can be either a graft, a graft with compressible attachment systems or a compressible stent. In this embodiment, system 30 preferably includes a deploying wire 36 which extends through channel 24 in catheter shaft 22. This configuration allows wire 36 to move axially along channel 24 in catheter shaft 22. An element for enabling actuation of system 30 comprises a generally ring-shaped knob 38, located at the proximal end of manipulating system 30. A plurality of elements 40 are provided, each of which is comprised of a flexible and resilient material, and is secured at an end 42 opposite a free end 44 of the distal end of wire 36. Preferably there are six elements 40 for secure gripping of prosthesis end 32. Elements 40 which are biased to an open or spread-out configuration which are adapted to include a tip 46, as shown in FIG. 12. Tip 46 operates to increase the gripping surface of element 40 as well as provide a surface for allowing secure and a traumatic engagement with a prosthesis. Tip 46 may be comprised of a material such as epoxy or any equivalent material which provides the system with the desired characteristics.

A bead 48 secures ends 42 of elements 40 to the distal end of wire 36, as shown in FIGS. 10–13. Bead 48 can be used to secure ends 42 to wire 36 by any conventional means including by utilizing epoxy. Alternatively, a tube 50 is secured to the distal end of wire 36, and extends about the secured ends 42 of elements 40 to crimp the joint between wire 36 and secured ends 42 of elements 40. A spring 52 extends between grip 28 and knob 38, and is compressed so as to normally bias system 30 in an unactivated condition as shown in FIG. 2, with released and expanded conditions shown in FIGS. 1, 3 and 4, and compressed condition shown in FIG. 5, wherein spring 52 is compressed and gripping elements 40 expand about graft end 32 for contracting thereabout to grip graft end 32.

As shown in FIGS. 6–9, a second preferred embodiment of catheter 20 and system 30 may include a folded balloon 54, extending from the distal end of wire 36, for stabilizing graft 34 and enabling improved gripping of graft end 32. A third preferred embodiment as shown in FIGS. 10 and 13 includes a further gripping element 56, which extends separately through shaft 22 and is maneuverable by the user separate from elements 40 to releasably grip graft end 32.

By way of example, the following describes a method of repositioning the end of a prosthesis using the method comprising the present invention for intraluminal gripping and manipulating of the graft. First, a patient is prepared in a conventional manner, and catheter 20 is directed to the repair site in the corporeal lumen adjacent prosthesis end 32.

As shown in FIGS. 2–5, jacket 26 is retracted from its initial position enclosing elements 40 by pulling grip 28 towards knob 38 against the biasing force of spring 52, so as to release elements 40 to expand outwardly from their enclosed position. Contemporaneously, catheter 20 is advanced until prosthesis end 32 is engaged by elements 40 by pushing on knob 38 and grip 28.

Next, jacket 26 is advanced to partially encapsulate elements 40 and compress tips 46 onto prosthesis end 32, by releasing grip 28 such that spring 52 causes grip 28 and jacket 26 to advance, enabling repositioning and adjusting of prosthesis end 32 to the desired location. Jacket 26 may then be retracted by pulling grip 28 towards knob 38, enabling elements 40 to resiliently expand and disengage from prosthesis end 32. Then jacket 26 may be advanced by releasing grip 28, whereby spring 50 pushes grip 28, and jacket 26 forward, to compress and enclose elements 40, enabling removal of catheter 20 from the corporeal lumen.

In the embodiment shown in FIGS. 6–10 and 13, balloon 54 increases the gripping force of system 30 on prosthesis end 32, with balloon 54 serving as a reactionary support for gripping elements 40 in engaging prosthesis end 32. Maneuverable element 56, in the embodiment shown in FIGS. 10 and 13, reaches and accesses areas between graft 34 and the lumen wall in addition to areas accessed by elements 40.

While several particular forms of the invention have been illustrated and described, it will be apparent that various modifications can be made without departing from the spirit and scope of the invention. For example, references to materials of construction and specific dimensions are also not intended to be limiting in any manner and other materials and dimensions could be substituted and remain within the spirit and scope of the invention. Accordingly, it is not intended that the invention be limited, except as by the appended claims.

What is claimed is:

1. An apparatus for manipulating a prosthesis, comprising
a catheter including a shaft having a proximal and distal ends, wherein the catheter shaft includes an enlarged portion at the distal end thereof;
an elongated device including a shaft having a proximal and distal ends disposed within the catheter;
a plurality of atraumatic gripping members on the distal end of the elongated device shaft and configured to fully retract within the enlarged portion of the catheter shaft;
an actuator located at the proximal end of the catheter; shaft which operated the plurality of atraumatic gripping members; and
a folded balloon, located at the catheter distal end of the catheter shaft, about which the plurality of atraumatic gripping members extend, adapted to releasably engage the end of the prosthesis.

2. The apparatus of claim 1, wherein the end of the prosthesis is compressible, and the plurality of atraumatic gripping members are further adapted to compress and grip the prosthesis compressible end for gripping thereof.

3. The apparatus of claim 1, wherein the catheter shaft is configured to enable insertion of the catheter into the corporeal lumen to a position at the repair site proximate to the end of the prosthesis.

4. The apparatus of claim 1, wherein the actuator comprises a knob proximate the proximal end of the catheter shaft for enabling the user to move the actuator relative to the knob and expand the plurality of atraumatic gripping members into the expanded state.

5. The apparatus of claim 1, wherein the actuator includes a deploying wire extending through the catheter shaft, including proximal and distal ends, and an actuating member secured to the deploying wire proximal end, and wherein the plurality of atraumatic gripping members are secured to the distal end of the actuating member.

6. The apparatus of claim 1, further comprising a spring configured to bias the actuator relative to the catheter shaft such that the plurality of atraumatic gripping members are normally in the contracted state.

7. The apparatus of claim 1, further comprising a grip attached to the proximal end of the catheter shaft.

8. The apparatus of claim 1, further comprising a tube connected to the distal end of the catheter shaft and to each of the plurality of atraumatic gripping members.

9. The apparatus of claim 1, wherein each atraumatic gripping member includes a tip comprised of epoxy.

10. The apparatus of claim 1, wherein the plurality of atraumatic gripping members comprise six atraumatic gripping members.

11. The apparatus of claim 1, further comprising a maneuverable gripping member, adapted to releasably grip the end of the prosthesis.

12. The apparatus of claim 1, wherein the plurality of atraumatic gripping members include a plurality of bulbous tips.

13. A method of manipulating the end of a prosthesis located at a repair site in a corporeal lumen, comprising the steps of:
introducing a catheter which includes a shaft having proximal and distal ends, a plurality of atraumatic gripping members adapted for gripping the end of the prosthesis located in the distal end of the catheter shaft, an actuator configured to move the plurality of atraumatic gripping members between an expanded state and a contracted state, to the repair site of the corporeal lumen, and a folded balloon located at the catheter distal end, about which the plurality of atraumatic gripping members extend;
moving the balloon into a releasable engagement with the end of the prosthesis;
actuating the plurality of atraumatic gripping members to grip the end of the prosthesis;
manipulating the plurality of gripping members to manipulate the end of the prosthesis; and
terminating the manipulating and gripping of the end of the prosthesis.

14. The method of claim 13, wherein the actuator includes a knob proximate the proximal end of the catheter shaft and other components and the step of actuating the plurality of gripping members comprises moving the other components of the actuator relative to the knob for extending and expanding the plurality of atraumatic gripping members into the expanded state.

15. The method of claim 13, wherein the actuator includes a deploying wire including proximal and distal ends, extending through the catheter shaft, and an actuating member secured to the deploying wire proximal end, and wherein the plurality of atraumatic gripping members are secured by the actuating member distal end, and the step of actuating the plurality of gripping members comprises pushing and releasing the actuating member and deploying wire.

16. The method of claim 13, wherein the catheter further comprises a tube secured to the plurality of atraumatic gripping members and to the actuator located in the catheter shaft proximate the catheter distal end, and the step of actuating the plurality of gripping members comprises sliding the tube to release the plurality of atraumatic gripping members.

17. The method of claim 13 wherein the step of actuating the plurality of atraumatic gripping members comprises releasing the plurality of atraumatic gripping members to expand into the expanded state about the end of the prosthesis, and contracting the plurality of atraumatic gripping members into the contracted state and grip the end of the prosthesis.

18. The method of claim 13, wherein the catheter shaft includes an enlarged portion at the distal end thereof, further comprising the step of retracting the plurality of atraumatic gripping members in the catheter shaft enlarged portion, to enable insertion of the catheter into the corporeal lumen to the position at the repair site proximate to the end of the prosthesis.

* * * * *